(12) United States Patent
Shalaby et al.

(10) Patent No.: US 8,858,595 B2
(45) Date of Patent: *Oct. 14, 2014

(54) BIOSWELLABLE SUTURES

(75) Inventors: Shalaby W. Shalaby, Anderson, SC (US); James M. Lindsey, III, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 682 days.

This patent is subject to a terminal disclaimer.

(21) Appl. No.: 11/596,545

(22) PCT Filed: Jun. 14, 2006

(86) PCT No.: PCT/US2006/022971
§ 371 (c)(1),
(2), (4) Date: Nov. 15, 2006

(87) PCT Pub. No.: WO2006/138300
PCT Pub. Date: Dec. 28, 2006

(65) Prior Publication Data
US 2008/0089840 A1 Apr. 17, 2008

Related U.S. Application Data

(63) Continuation-in-part of application No. 11/453,207, filed on Jun. 14, 2006.

(60) Provisional application No. 60/741,329, filed on Dec. 1, 2005, provisional application No. 60/690,751, filed on Jun. 15, 2005.

(51) Int. Cl.
*A61L 17/10* (2006.01)

(52) U.S. Cl.
USPC .................... 606/230; 606/228; 424/400

(58) Field of Classification Search
None
See application file for complete search history.

(56) References Cited

U.S. PATENT DOCUMENTS

| 3,991,766 | A | * | 11/1976 | Schmitt et al. | 606/230 |
|---|---|---|---|---|---|
| 4,857,602 | A | * | 8/1989 | Casey et al. | 525/408 |
| 5,320,624 | A | | 6/1994 | Kaplan et al. | |
| 6,485,749 | B1 | * | 11/2002 | Shalaby | 424/486 |
| 2003/0162940 | A1 | | 8/2003 | Shalaby | |
| 2004/0167575 | A1 | * | 8/2004 | Roby | 606/228 |
| 2005/0038472 | A1 | * | 2/2005 | Furst | 606/228 |

OTHER PUBLICATIONS

Wang et al. Journal of Macromolecular Science, Part A: Pure and Applied Chemistry, 35(5), p. 811-820, 1998.*
Cai et al. Polymer 43, p. 3585-3591, 2002.*
Miller et al., Surgery, 10 (2), 156, 1987.

* cited by examiner

*Primary Examiner* — Nissa Westerberg

(57) ABSTRACT

Bioswellable sutures are provided in the form of absorbable, compliant monofilaments of an amphiphilic copolyester, an absorbable multifilament braid, a non-absorbable monofilament with swellable outer layer, a non-absorbable multifilament braid with an absorbable monofilament core of an amphiphilic copolymer, and a non-absorbable, multifilament braid molecularly integrated with an outer sheath that is highly hydrophilic.

12 Claims, No Drawings

BIOSWELLABLE SUTURES

FIELD OF THE INVENTION

This invention relates to bioswellable surgical sutures that undergo swelling when placed in the biological environment, resulting in an increase in their cross-sectional area of at least 20 percent. Clinically, the bioswellable sutures minimize the traditional disparity between the needle and suture cross-sectional areas and subsequently, reduce the needle-hole leakage and associated blood loss, delay in hemostasis, and risk of infection. The bioswellable sutures, as described in this invention, are presented as preferred or superior alternatives to those commonly used in surgery, and specifically, in the case of colorectal, cardiovascular, laparoscopic, and microsurgical procedures.

BACKGROUND OF THE INVENTION

Most mechanical ligations of living tissues using surgical sutures require a combination of a thread and needle. In most cases, the needle diameter far exceeds that of the suture and the needle-to-suture diameter can be as high as 2:1 or 3:1. This can result in leakage of bodily fluids, including blood, through needle-created holes about implanted suture thread. Depending on the surgical site, this can lead to bleeding and infection. A few attempts have been made in earlier decades to minimize needle hole leakage without achieving a clinically optimum solution.

In a study by C. M. Miller and coworkers [*Surgery*, 10(2), 156 (1987)] on reduced anastomotic bleeding and reduction of blood loss from a vascular anastomosis when one is using an expanded polytetrafluoroethylene (ePTFE) graft, two sutures were used, one made of ePTFE and the other of polypropylene, which were designed to have a needle-to-suture diameter ratio of about 1:1. Theoretically, this allows the suture to completely fill the graft needle hole and control bleeding. These sutures were evaluated in a heparin-treated, canine in vivo model to measure graft needle-hole bleeding. Results of the study, along with subjective evaluations of the sutures' handling qualities led to the conclusion that sutures produced with needle-to-suture ratios of 1:1 greatly reduce graft needle-hole bleeding and will be a useful addition to the vascular surgeon's armamentarium.

In an approach to prevent needle-hole bleeding during vascular anastomosis using expanded polytetrafluoroethylene (ePTFE) grafts treated with sealants, investigators of the prior art noted that Fibrin Glue (FG) is more effective than a thrombin-soaked gelatin sponge for achieving hemostasis of needle- or suture-hole bleeding. However, the risk of infection associated with these naturally derived sealants was not ruled out.

Fibrin glue is frequently used to seal and cover the anastomoses in many operations. However, in the case of gastrointestinal surgeries, the anastomoses are potentially contaminated and FG may promote bacterial growth, thus increasing the risk of leakage The above-noted accounts of the prior art dealing with different approaches to minimize suture- or needle-hole bleeding or leakage and associated undesirable outcomes illustrate the limited success of the prior art investigators in providing a clinically optimum solution to this problem. This prompted the pursuit of the present invention which deals with the development of a broad range of novel, bioswellable, absorbable and non-absorbable sutures, which can be used more effectively in minimizing or eliminating suture- or needle-hole leakage under the prevailing conditions of several surgical procedures.

SUMMARY OF THE INVENTION

This invention deals, in general, with bioswellable surgical sutures which undergo at least 20 percent increase in their cross-sectional area when placed in a biological environment. One specific aspect of this invention deals with a bioswellable suture comprising a compliant monofilament comprising an absorbable polyether-ester, the monofilament having a tensile modulus of less than about 400 Kpsi and exhibiting an at least 20 percent increase in cross-sectional area and an at least 5 percent decrease in tensile modulus when placed in a biological environment, wherein the polyether-ester comprises a polyether glycol end-grafted with at least one cyclic monomer selected from the group consisting of l-lactide, glycolide, p-dioxanone, trimethylene carbonate, $\epsilon$-caprolactone, 1,5-dioxepan-2-one and a morpholinedione, and wherein the polyether glycol is selected from the group consisting of polyethylene glycol, polypropylene glycol, and block copolymers of ethylene glycol and propylene glycol. Preferably, the polyether glycol is a solid polyethylene glycol having a molecular weight of greater than about 8 kDa and more preferably, the polyethylene glycol comprises at least about 10 weight percent of the total polyether-ester mass. It is also preferred that the bioswellable suture further comprising a surface coating on the monofilament, wherein the surface coating comprises at least about 0.01 weight percent of total mass of the suture, wherein the surface coating comprises an $\epsilon$-caprolactone copolymer. Preferably, the surface coating contains at least one bioactive agent selected from the group consisting of antimicrobial agents, anti-inflammatory agents, and antineoplastic agents, the coated monofilament being capable of retaining at least about 40 percent of its initial breaking strength after placing in the biological environment for four days.

Another specific aspect of this invention deals with a bioswellable suture comprising a compliant monofilament comprising a core layer and an outer layer molecularly integrated with the core layer, the outer layer comprising highly hydrophilic moieties derived from grafts of at least one unsaturated monomer selected from the group consisting of hydroxyethyl methacrylate, maleic anhydride, itaconic anhydride, and methacrylic acid, the monofilament having a tensile modulus of less than about 400 Kpsi and exhibiting an at least 20 percent increase in cross-sectional area and an at least 5 percent decrease in tensile modulus when placed in a biological environment, wherein the core comprising a non-absorbable polymer selected from the group consisting of isotactic polypropylene, an aliphatic polyamide, and a segmented copolyester, preferably comprising polytetramethylene terephthalate. It is also preferred that the outer layer of the aliphatic polyamide core comprises a polyethylene oxide graft. It is most preferred that the outer layer of the compliant monofilament suture contains at least one bioactive agent selected from the group consisting of anti-inflammatory agents, antimicrobial agents, and antineoplastic agents.

A key aspect of this invention deals with a bioswellable suture exhibiting an at least 20 percent increase in cross-sectional area and an at least 5 percent decrease in tensile modulus when placed in a biological environment, wherein the suture comprising a braided non-absorbable multifilament encased in a molecularly integrated, highly swellable sheath, comprising a highly hydrophilic moieties derived from grafts of at least one monomer selected from the group consisting of hydroxyethyl methacrylate, maleic anhydride, itaconic anhydride, and methacrylic acid, itaconic anhydride.

Another key aspect of this invention deals with a bioswellable suture comprising an absorbable monofilament core and a non-absorbable multifilament braided sheath, the core comprising polyethylene glycol end-grafted with at least one monomer selected from the group consisting of l-lactide, glycolide, trimethylene carbonate, p-dioxanone, 1,5-dioxepan-2-one, $\epsilon$-caprolactone, and a morpholinedione, the sheath comprising a heterochain polymer selected from the group consisting of Nylon 6, Nylon 66, polyethylene terephthalate, polybutylene terephthalate, polytrimethylene terephthalate, segmented copolymers of polyalkylene terephthalate and polytetramethylene glycol, wherein the bioswellable suture further comprising a surface coating comprising a $\epsilon$-caprolactone/glycolide copolymer or a polyethylene glycol end-grafted with a mixture of $\epsilon$-caprolactone and glycolide.

A special aspect of this invention deals with a bioswellable braided multifilament suture comprising an absorbable polyether-ester, the individual filaments exhibiting at least 5% increase in cross-sectional area when placed in the biological environment, wherein the polyether-ester comprises a polyether glycol end-grafted with at least one cyclic monomer selected from the group consisting of l-lactide, glycolide, p-dioxanone, trimethylene carbonate, $\epsilon$-caprolactone, 1,5-dioxepan-2-one and a morpholinedione, and wherein the suture further comprises a surface coating comprising an $\epsilon$-caprolactone copolymer.

DETAILED DESCRIPTION OF PREFERRED EMBODIMENTS

This invention deals with a broad range of new, absorbable and non-absorbable, compliant, bioswellable sutures that are designed to satisfy unmet clinical requirements associated with (1) minimizing or eliminating suture- or needle-hole bleeding and blood loss in surgical procedures involving highly vascularized tissues and particularly, in the case of vascular anastomosis where low tear strength and/or microporous synthetic vascular grafts or patches are used; and (2) minimizing or eliminating suture- or needle-hole leakage and risk of infection encountered during gastrointestinal and colorectal surgeries. The bioswellable sutures, subject of this invention, can be presented as preferred alternatives to more conventional sutures and particularly, those used in the area of (1) ophthalmic and/or plastic surgery; (2) laparoscopic surgery, and (3) tissue engineering.

The bioswellable sutures can be in the form of (1) an absorbable, compliant monofilament comprising an amphiphilic copolyester; (2) a non-absorbable monofilament with swellable outer layer; (3) a non-absorbable multifilament braid with an absorbable monofilament core comprising an amphiphilic copolymer; and (4) a non-absorbable, multifilament braid molecularly integrated with an outer sheath that is highly hydrophilic.

An important general aspect of this invention deals with two types of absorbable, bioswellable monofilament sutures having fast- and slow-absorption and breaking strength retention (BSR) profiles, not only as novel sutures for new applications, but also as preferred alternatives to several commercial sutures, including the only two available ones which were developed, specifically, to address the suture- or needle-hole bleeding. Clinical attributes of the bioswellable, absorbable monofilament sutures, subject of this invention, are discussed in the following paragraphs and their advantages over competitive commercially available sutures are also noted.

In a review by P. Hogston [*The Obstetrician & Gyneacologist*, 3(3), 127 (2001)] on suture choice in general gynecological surgery, the author analyzed many of the issues that need further attention toward improving the performance and clinical efficacy of surgical sutures while minimizing or eliminating a number of undesirable outcomes. Issues pertinent to the present invention are those dealing with (1) the fact that as of 1990, 66 percent of the surgeons used catgut sutures and only 33 percent used synthetic sutures in the closure of the vaginal vault at hysterectomy, because of catgut suture's relatively fast absorption, ease of handling, and associated knot security—this is in spite of the marginal breaking strength and frequently acknowledged high tissue reaction encountered with catgut sutures compared with their synthetic counterparts; (2) preferred use of synthetic, absorbable sutures with delayed absorption profile in incontinence surgery—these sutures were preferred over the easier-to-handle catgut because of their delayed absorption; (3) the fact that as of 1990, rapidly absorbable sutures were widely used in prolapse surgery, but as many as 30 percent of the operations were repeat procedures—this and subsequent studies justified the preferred use of synthetic sutures having a delayed absorption profile in prolapse surgery; and (4) the limited use of microporous polytetra-fluoroethylene (ePTFE, Gore-Tex®) as a non-absorbable suture in reconstructive gynecological surgery to decrease suture-line bleeding, in spite of its problematic knot security (at least seven throws are required) and the risk of infection generally associated with non-absorbable sutures. Accordingly, there exists a definite need for new synthetic absorbable sutures having (1) the attributes of catgut in terms of ease of handling and knot security, but free of their undesirable high tissue reactions and marginal breaking strength, for use in the closure of the vaginal vault at hysterectomy—the proposed high strength, amphiphilic, fast absorbing, compliant, bioswellable sutures, which undergo further increase in compliance in the biologic environment to provide optimum knot security, are likely to be preferred alternatives to catgut suture in this application; (2) delayed absorption can be presented as preferred alternatives to catgut and rapidly absorbing polyglycolide sutures for use in incontinence surgery, using a similar rationale to that presented above—the amphiphilic, high strength, slow-absorbing, compliant, bioswellable sutures, subject of this invention, which undergo further increase in compliance in the biologic environment to provide optimum knot security, are likely to meet the requirements of the new alternative sutures to both catgut and polyglycolide sutures; (3) delayed absorption can be used as preferred substitutes for rapidly absorbable sutures for use in prolapse surgery—the proposed amphiphilic, high strength, slow-absorbing, compliant, bioswellable sutures, which undergo further increase in compliance to provide optimum knot security are likely to meet the requirements of such new sutures; (4) delayed absorption and non-porous, surface-coated (with lubricious copolymer) sutures can be presented as preferred alternatives to Gore-Tex® sutures for use in reconstructive gynecological surgery as they are expected to have improved tie-down characteristics, higher knot security, and a much lower risk of infection—absorbable sutures are associated with lower risk of infection than their non-absorbable counterparts. Collectively, the two types of bioswellable, absorbable sutures (fast- and slow-absorbing), subject of this invention, are expected to present the general gynecological surgeon with preferred alternatives to currently used sutures in their area of clinical practice.

Fibrin glue (FG) is frequently used to seal and cover the anastomoses in many operations. However, in the case of gastrointestinal surgeries, the anastomoses are potentially contaminated and FG may promote bacterial growth, thus increasing the risk of leakage. Bioswellable, slow-absorbing sutures and preferably those containing an antimicrobial agent in their coating may prevent leakage through needle/suture holes, which will help in managing potential infection.

Cited in the prior art is a study on reducing the incidence and managing the consequences of anastomotic leakage after rectal resection, the investigators noted that anastomotic dehiscence is a serious, life-threatening complication of any rectal anastomosis and may be associated with an increased risk of rectal cancer recurrence. In this respect, the coated, slow-absorbing, bioswellable sutures, capable of the controlled delivery of antimicrobial agents, subject of this invention, can be presented as superior alternatives to traditional sutures. The bioswellable sutures will be capable of preventing needle bleeding and leakage of potential infected intestinal contents while prophylactically managing infection at the suture line.

Contrasting the bioswellable, absorbable, monofilament sutures, subject of this invention, with the commercial, non-absorbable sutures known in the trade as Gore-Tex® and HemoSeal®, as outlined below, justifies denoting the absorbable, bioswellable sutures as their preferred alternatives.

Although both the tapered polypropylene suture-needle combination (Hemo-seal®) and expanded polytetrafluoroethylene suture (Gore-Tex®) have been accepted by a number of vascular surgeons, these sutures do suffer from a number of limitations. These include (1) diminished breaking strength at the tapered segment of the Hemo-seal; (2) the compromised needle pull strength in Hemo-seal; (3) the surface porosity of Gore-Tex, which may harbor microorganisms leading to infection; (4) the poor tie-down characteristics of the Gore-Tex suture; (5) the breaking strength of an unknotted and knotted ePTFE suture is significantly less than most clinically accepted sutures; (6) the poor knot security of Gore-Tex® and the need to use at least seven throws; (7) tendency of Gore-Tex® to creep during suturing and lose its ability to recover its original uncompressed large diameter; (8) poor tear strength of Gore-Tex® and possible production of delaminated PTFE fragments; and (9) the high number of Gore-Tex throws and high inherent modulus and stiffness of PTFE as a polymer, can lead to a high degree of biomechanical incompatibility, which, in turn, may increase tissue reaction and likelihood of infection.

The swellable, absorbable sutures, subject of this invention are designed to help minimize suture line bleeding, and the unique chemical structure of their polymers allows the needle attachment to its monofilament suture thread, which expands radially, immediately after application, to fill the needle hole. This is expected to reduce blood loss and shorten time to hemostasis.

Interest of the surgical community as well as patients in minimally invasive surgical procedures and subsequent reliance on laparoscopic techniques has grown significantly over the past two decades. A number of recent applications testifying to this trend have focused on the successful use of laparoscopy in a broad range of areas, including (1) treatment of morbid obesity; (2) surgery for colon cancer; (3) radical cystectomy with continent urinary diversion; (4) myomectomy for symptomatic uterine myomas; and (5) surgical management of invasive cervical cancer.

Laparoscopic surgery has developed out of multiple technology innovations. In the treatment of morbid obesity, several surgical procedures are currently available, including gastric bypass, bilio-pancreatic diversion (BPD) with duodenal switch, and the adjustable gastric band. These operations may be performed using laparoscopic surgical techniques to minimize peri-operative morbidity and postoperative recovery time. Good evidence exists for the laparoscopic approach for colon cancer patients with outcomes comparable to open surgery. Laparoscopic radical cystectomy with urinary diversion has evolved rapidly throughout the past decade. Short-term data have shown that this is a feasible technique that respects the basic principles of surgical oncology. However, the possibility of decreased blood loss, improved visualization, shorter hospital stay, and less postoperative pain are balanced against technical difficulty, long operative times, and unproved long-term efficacy compared with the open gold standard. Laparoscopy has been a long-standing technique for gynecologic surgery with increasing shifts toward total laparoscopic hysterectomies, myomectomies, and for staging of gynecologic cancers. As laparoscopic instrumentation becomes more advanced, there will be greater application in a wide range of procedures traditionally performed open. More importantly, historical sutures that are now being utilized in laparoscopic surgery are done in the absence of comparable data to verify efficacy. This would apply to the handling of suture with laparoscopic instruments which can fray monofilament sutures, less than optimal knot security in the setting of intra- and extracorporeal knot tying, memory and handling issues that may influence insertion through the trocars and ability to suture tissue. In short, the inherent loss of tactile capability and handling as compared to open surgery and the paradigm shift toward laparoscopy will inevitably increase the need to develop suture material which reproduce the handling and knot security that have historically been developed for open surgical procedures.

Contrasting the growing significance of laparoscopic surgery with the limitations associated with presently used sutures in common, open procedures makes a compelling case to explore the use of bioswellable absorbable sutures, subject of this invention, because of their many integrated attributes. These include (1) their expected ability to prevent needle hole bleeding; (2) having a broad range of tailored absorption and strength retention profiles to meet the requirements of specific surgical procedures; (3) being compliant and becoming more compliant in the biological environment; (4) having high breaking strength, while being easy-to-handle and providing exceptional knot security; and (5) being available in microsurgical sizes.

Interest in plastic surgery and microsurgical procedures has grown significantly over the past two decades and is expected to continue at a faster rate in the forthcoming years. For both areas, where absorbable sutures are most useful, suture line bleeding and interfering with hemostasis are major concerns. And limitation associated with the use of common sizes of absorbable monofilament sutures having limited range of absorption and strength profile evokes the need to explore the use of the bioswellable, absorbable sutures having the unique properties outlined in the previous paragraph. More importantly is the fact that the bioswellable sutures can be and have been produced in our laboratory in sizes corresponding to about 70 micron in diameter. Additionally, these microsutures can undergo swelling in saline at room temperature to more than 70 percent of their original cross-sectional area.

In his review of articular cartilage injuries of the knee, and specifically the use of autogenous cartilage implantation as a treatment option, A. F. LaPrade and colleagues [*Physicians & Sports Medicine,* 29, 53 (2001)] described the preparation of the patient's own chondrocytes for implantation at the site of the articular cartilage defect. Implantation of these cells requires an open incision, similar to the incision for a total knee replacement procedure, and arthrotomy. The articular cartilage lesion is isolated, and all degenerative cartilage debrided. Scar tissue is removed from the bed of the defect. The size of the articular cartilage defect is then templated, and a matching piece of periosteum is harvested from the distal femur or the proximal tibia. The free piece of periosteum is microsutured into the edges of the defect; it is essential to obtain a watertight seal. Then, fibrin glue is placed around the edges of the suture line to further insure that cells do not leak through the suture holes. The prepared implantation cells are then injected under the periosteal patch. The injection site is closed with a suture and fibrin glue.

This is a excellent illustration of the importance of minimizing suture hole leakage in the growing area of tissue engineering, which is beyond the traditional surgical procedure where sutures are routinely used.

This invention deals, in general, with bioswellable surgical sutures which undergo at least 20 percent increase in their cross-sectional area when placed in a biological environment. One specific aspect of this invention deals with a bioswellable suture comprising a compliant monofilament comprising an absorbable polyether-ester, the monofilament having a tensile modulus of less than about 400 Kpsi and exhibiting an at least 20 percent increase in cross-sectional area and an at least 5 percent decrease in tensile modulus when placed in a biological environment, wherein the polyether-ester comprises a polyether glycol end-grafted with at least one cyclic monomer selected from the group consisting of l-lactide, glycolide, p-dioxanone, trimethylene carbonate, $\epsilon$-caprolactone, 1,5-dioxepan-2-one and a morpholinedione, and wherein the polyether glycol is selected from the group consisting of polyethylene glycol, polypropylene glycol, and block copolymers of ethylene glycol and propylene glycol. Preferably, the polyether glycol is a solid polyethylene glycol having a molecular weight of greater than about 8 kDa and more preferably, the polyethylene glycol comprises at least about 10 weight percent of the total polyether-ester mass. It is also preferred that the bioswellable suture further comprising a surface coating on the monofilament, wherein the surface coating comprises at least about 0.01 weight percent of total mass of the suture, wherein the surface coating comprises an $\epsilon$-caprolactone copolymer. Preferably, the surface coating contains at least one bioactive agent selected from the group consisting of antimicrobial agents, anti-inflammatory agents, and antineoplastic agents, the coated monofilament being capable of retaining at least about 40 percent of its initial breaking strength after placing in the biological environment for four days.

Another specific aspect of this invention deals with a bioswellable suture comprising a compliant monofilament comprising a core layer and an outer layer molecularly integrated with the core layer, the outer layer comprising highly hydrophilic moieties derived from grafts of at least one unsaturated monomer selected from the group consisting of hydroxyethyl methacrylate, maleic anhydride, itaconic anhydride, and methacrylic acid, the monofilament having a tensile modulus of less than about 400 Kpsi and exhibiting an at least 20 percent increase in cross-sectional area and an at least 5 percent decrease in tensile modulus when placed in a biological environment, wherein the core comprising a non-absorbable polymer selected from the group consisting of isotactic polypropylene, an aliphatic polyamide, and a segmented copolyester, preferably comprising polytetramethylene terephthalate. It is also preferred that the outer layer of the aliphatic polyamide core comprises a polyethylene oxide graft. It is most preferred that the outer layer of the compliant monofilament suture contains at least one bioactive agent selected from the group consisting of anti-inflammatory agents, antimicrobial agents, and antineoplastic agents.

A key aspect of this invention deals with a bioswellable suture exhibiting an at least 20 percent increase in cross-sectional area and an at least 5 percent decrease in tensile modulus when placed in a biological environment, wherein the suture comprising a braided non-absorbable multifilament encased in a molecularly integrated, highly swellable sheath, comprising a highly hydrophilic moieties derived from grafts of at least one monomer selected from the group consisting of hydroxyethyl methacrylate, maleic anhydride, itaconic anhydride, and methacrylic acid, itaconic anhydride.

Another key aspect of this invention deals with a bioswellable suture comprising an absorbable monofilament core and a non-absorbable multifilament braided sheath, the core comprising polyethylene glycol end-grafted with at least one monomer selected from the group consisting of l-lactide, glycolide, trimethylene carbonate, p-dioxanone, 1,5-dioxepan-2-one, $\epsilon$-caprolactone, and a morpholinedione, the sheath comprising a heterochain polymer selected from the group consisting of Nylon 6, Nylon 66, polyethylene terephthalate, polybutylene terephthalate, polytrimethylene terephthalate, segmented copolymers of polyalkylene terephthalate and polytetramethylene glycol, wherein the bioswellable suture further comprising a surface coating comprising a $\epsilon$-caprolactone/glycolide copolymer or a polyethylene glycol end-grafted with a mixture of $\epsilon$-caprolactone and glycolide.

Further illustrations of the present invention are provided by the following examples:

EXAMPLE 1

Two-step Synthesis of Amphiphilic Polyether-Esters and Their Characterization (PI Series): General Methods The first step of the two-step method entails end-grafting high molecular polyethylene glycol (PEG) with trimethylene carbonate (TMC) in the presence of stannous octanoate as the catalyst, at a selected temperature range until an almost complete consumption of TMC is achieved. In the second step, one or more cyclic monomer(s) are then mixed with the TMC-end-grafted PEG. The reaction is continued to completion at a selected temperature range. Thirteen typical polymers (PI-F-1 to PI-F-4 and PI-S-1 to PI-S-9) were prepared using this general protocol and following the experimental scheme outlined below for their synthesis and characterization.

Predried crystalline, PEG-35 (mol. Wt.=35 kDa) was mixed, under nitrogen in a stainless steel reactor equipped for mechanical stirring, with the desired amount of trimethylene carbonate monomer in the presence of stannous octanoate as a catalyst. The mixture was heated and stirred to achieve complete dissolution of all reactants. The mixing was continued while heating to a polymerization temperature of 140° C. or 150° C. depending on the composition. The reaction was maintained at that temperature while stirring until essentially complete monomer conversion was achieved (~0.5-1.5 hours depending on the monomer concentration). A charge of cyclic monomer(s) was then added and the mixture stirred to achieve complete dissolution of all reactants (mixing temperatures of 110° C., 140° C. or 150° C. were used depending on the composition). The mixing was continued while heating to a polymerization temperature of 160° C., 170° C., or 180° C., depending on the type and concentration of cyclic monomer(s). The reaction was maintained at that temperature while stirring until the product became too viscous to stir and essentially complete monomer conversion was achieved (7-12 hours depending on the type and concentration of cyclic monomer(s)). At this stage, polymerization was discontinued, the product was cooled, isolated, ground, dried, and traces of residual monomer were removed by distillation under reduced pressure using a temperature that is below the copolymer melting temperature ($T_m$), but not exceeding 110° C.

The resulting dry copolymers were characterized for identity and composition (IR, NMR), thermal properties, namely $T_m$ and $\Delta H_f$ (DSC), molecular weight in terms of inherent viscosity (solution viscometry in CHCl$_3$ or hexafluoroisopropyl alcohol), or number/weight average molecular weight (GPC), and melt viscosity (melt rheometer). The $\Delta H_f$ is used as an indirect measure of percent crystallinity. Pertinent polymerization charge/conditions and analytical data are summarized in Tables I and II.

EXAMPLE 2

One-Step Synthesis of Amphiphilic Polyether-Esters and Their Characterization (PII Series): General Method The copolymers were prepared using a one-step scheme. This entailed direct end-grafting of high molecular weight PEG with one or more monomer(s). the reaction conditions were similar to those used in the second-step of the two-step scheme of Example 1. Copolymer isolation and purification/drying were conducted as described in Example 1. Five typical polymers (PII-F-1 to PII-F-4 and PII-S-1) were prepared using the general protocol. Pertinent reaction polymerization charge/conditions and analytical data are outlined in Tables III and IV.

TABLE I

Synthesis and Properties of Type PI Fast-Absorbing Amphiphilic Polyether-esters (PI-F-1 to PI-F-4)

| | | Composition of Charge | | | | DSC Data | |
|---|---|---|---|---|---|---|---|
| Polymer Number | PEG $M_n$, kDa | PEG/TMC/ Polyester, (wt) | Polyester Monomer Types & molar ratios[a] | Catalyst M/C[b] | I.V.[c] | $T_m$, °C. | $\Delta H_f$, J/g |
| PI-F-1 | 35 | 20/5/75 | 80/20 G/CL | 6000 | 1.38 | 218 | 72 |
| PI-F-2 | 35 | 20/5/75 | 90/10 G/TMC | 6000 | 1.13 | — | — |
| PI-F-3 | 35 | 25/2/73 | 87/13 G/TMC | 6000 | — | — | — |
| Pl-F-4 | 35 | 25/2/73 | 75/25 G/CL | 6000 | 1.53 | 60, 222 | 22, 52 |

[a]G = Glycolide; CL = ε-caprolactone; TMC = trimethylenecarbonate.
[b]Molar ratio of monomer to stannous octanoate.
[c]Inherent viscosity in HFIP

TABLE II

Synthesis and Properties of Type PI Slow-Absorbing Amphiphilic Polyether-esters (PI-S-1 to PI-S-9)

| | | Composition of Charge | | | GPC[c] Data | | | DSC Data | |
|---|---|---|---|---|---|---|---|---|---|
| Polymer Number | PEG $M_n$, kDa | PEG/TMC/ Polyester, (wt) | Polyester Monomer Types & molar ratios[a] | Catalyst M/C[b] | Mn, kDa | Mw, kDa | I.V.[d] | Tm, °C. | $\Delta H_f$, J/g |
| PI-S-1 | 35 | 25/15/60 | 88/12 LL/G | 2000 | 48.0 | 82.9 | 1.16 | 53, 143 | 27, 22 |
| PI-S-2 | 35 | 28/12/60 | 95/5 LL/G | 4000 | 44.0 | 73.7 | 1.05 | 51, 145 | 32, 31 |
| PI-S-3 | 35 | 31/9/60 | 95/5 LL/G | 4000 | 39.9 | 64.1 | 1.00 | 51, 127 | 42, 15 |
| PI-S-4 | 35 | 31/2/67 | 95/5 LL/G | 3000 | 41.4 | 69.6 | 1.01 | 49, 146 | 21, 27 |
| PI-S-5 | 35 | 20/5/75 | 92/8 LL/G | 3000 | 91.0 | 128.2 | 1.23 | 154 | 34 |
| PI-S-6 | 35 | 27/3/70 | 100 LL | 2500 | 51.9 | 82.2 | 0.96 | 53, 172 | 14, 34 |
| PI-S-7 | 35 | 25/2/73 | 97/3 LL/TMC | 1800 | 56.0 | 164.8 | 0.92 | 160 | 30 |
| PI-S-8 | 35 | 20/2/78 | 96/4 LL/CL | 3000 | 101.4 | 198.9 | 1.52 | 46, 177 | 3, 47 |
| PI-S-9 | 35 | 23/2/75 | 96/4 LL/CL | 3000 | 99.6 | 187.4 | 1.28 | 165 | 33 |

[a]G = Glycolide; LL = l-lactide; TMC = trimethylene carbonate; CL = ε-caprolactone.
[b]Molar ratio of monomer to stannous octanoate.
[c]Gel permeation chromatography in CH$_2$Cl$_2$.
[d]Inherent viscosity in CHCl$_3$

TABLE III

Synthesis and Properties of Type PII Fast-Absorbing
Amphiphilic Polyether-esters (PII-F-1 to PII-F-4)

| | | Composition of Charge | | | | DSC Data | |
|---|---|---|---|---|---|---|---|
| Polymer Number | PEG $M_n$, kDa | PEG/ Polyester, (wt) | Monomer Types & molar ratios[a] | Catalyst M/C[b] | I.V.[c] | $T_m$, ° C. | $\Delta H_f$, J/g |
| PII-F-1 | 35 | 20/80 | 70/30 G/CL | 10000 | 1.32 | 58, 125, 219 | 15, 9, 44 |
| PII-F-2 | 35 | 18/82 | 70/30 G/CL | 8000 | 1.62 | 52, 128, 214 | 11, 6, 42 |
| PII-F-3 | 20 | 10/90 | 90/10 G/TMC | 8000 | 1.66 | 221 | 77 |
| PII-F-4 | 20 | 7/93 | 90/10 G/TMC | 12000 | 1.51 | 230 | 72 |

[a] G = Glycolide; CL = ε-caprolactone; TMC = trimethylenecarbonate.
[b] Molar ratio of monomer to stannous octanoate.
[c] Inherent viscosity in HFIP

TABLE IV

Synthesis and Properties of Type PII Slow-Absorbing
Amphiphilic Polyether-ester (PII-S-1)

| | | Composition of Charge | | | | DSC Data | |
|---|---|---|---|---|---|---|---|
| Polymer Number | PEG $M_n$, kDa | PEG/ Polyester, (wt) | Monomer Types & molar ratios[a] | Catalyst M/C[b] | I.V.[c] | $T_m$, ° C. | $\Delta H_f$, J/g |
| PII-S-1 | 35 | 37/63 | 97/3 LL/TMC | 2000 | 86.9 | 147.1 | 0.86 |

[a] LL = l-lactide; TMC = trimethylene carbonate; CL = ε-caprolactone.
[b] Molar ratio of monomer to stannous octanoate.
[c] Gel permeation chromatography in $CH_2Cl_2$.
[d] Inherent viscosity in $CHCl_3$

EXAMPLE 3

General Experimental Methods for Monofilament Spinning, Orientation, and In Vitro Testing For Melt Spinning—A ¾" single screw extruder is used. For a typical slow-absorbing copolymer, having a maximum Tm of about 150, the temperature profile used at the different zones of the extruder vary as follows: Zone 1, 125° C.; Zone 2, 149° C.; Zone 3, 175° C.; and Spinhead, 185° C.

For Orientation—The temperature and draw conditions noted in Section 5.1 will be applied using heated Godets.

For testing the properties of oriented monofilaments and then swelling behavior, (1) the initial tensile properties, breaking strength retention data of the monofilament sutures are determined using a MiniBionix MTS Universal Tester, Model 858; (2) the simulated bioswelling properties are evaluated using an optical micrometer on the sample incubated in a phosphate buffer at 37° C. and pH 7.2; and (3) the in vitro BSR data were determined on sutures incubated in a phosphate buffer at 37° C. and pH 7.2.

Polyether-esters PI-F-3, PI-F-4, PII-F-1, and PII-F-2 were converted to oriented monofilaments MI-F-3, MI-G-4, MII-F-1, and MII-F2 and polyether-esters PI-S-1, PI-S-5, PI-S-6, PI-S-7, PI-S-8, PI-S-9, and PII-S-1 were converted to oriented monofilaments MI-S-1, MI-S-5, MI-S-6, MI-S-7, MI-S-8, MI-S-9, and MII-S-1 and tested for their in vitro properties using the experimental procedures outlined above. Pertinent tensile properties, in vitro breaking strength retention (BSR), and swelling data are summarized in Tables V and VI.

TABLE V

Extrusion of Polyether-esters PI-F-3, PI-F-4, PII-F-1, and
PII-F-2 and Properties of Their Monofilaments as Sutures

| | Monofilament Number | | | |
|---|---|---|---|---|
| Properties | MI-F-3 | MI-F-4 | MII-F-1 | MII-F-2 |
| Copolymer used from Table 1 | PI-F-3 | PI-F-4 | PII-F-1 | PII-F-2 |
| Tensile properties | | | | |
| Diameter, mm | 0.37 | 0.43 | 0.40 | 0.43 |
| Linear strength, Kpsi (N) | 60.7 | 30.7 | 45.5 | 51.8 |
| | (44.4) | (30.0) | (46.3) | (51.9) |
| Modulus, Kpsi | 685 | 364 | 430 | 172 |
| Elongation, % | 38 | 38 | 28 | 53 |
| Knot strength, N | 28.1 | 28.1 | 23.5 | 31.9 |
| BSR[a], % @ Days 3, 7, 14, 21 | — | — | — | — |
| Cross-sectional increase, % at | | | | |
| 10 min. | — | — | — | — |
| 60 min. | — | — | — | 20[a] |
| 16 hrs. | — | — | — | — |

[a] Using phosphate buffer at pH 7.2 and 37° C.

TABLE VI

Extrusion of Polyether-esters PI-S-1, PI-S-5, PI-S-6, PI-S-7, PI-S-8, PI-S-9, and PII-S-1 and Properties of Their Monofilaments as Sutures

| Properties | Monofilament Number | | | | | | |
|---|---|---|---|---|---|---|---|
| | MI-S-1 | MI-S-5 | MI-S-6 | MI-S-7 | MI-S-8 | MI-S-9 | MII-S-1 |
| Copolymer used from Table II | PI-S-1 | PI-S-5 | PI-S-6 | PI-S-7 | PI-S-8 | PI-S-9 | PII-S-1 |
| | Tensile properties | | | | | | |
| Diameter, mm | 0.13 | 0.22 | 0.23 | 0.36 | 0.47 | 0.29 | 0.10 |
| Linear strength, Kpsi (N) | 45.9 | 46.3 | 47.7 | 32.9 | 46.1 | 46.2 | 34.5 |
| | (4.2) | (12.13) | (15.9) | (23.5) | (55.6) | (20.7) | (1.87) |
| Modulus, Kpsi | 239 | 376 | 453 | 397 | 315 | 345 | 190 |
| Elongation, % | 44 | 73 | 73 | 57 | 90 | 91 | 99 |
| Knot strength, N | 2.64 | 12.3 | 16.3 | 23.4 | 47.6 | 17.3 | — |
| BSR$^a$, % @ Days 3, 7, 14, 21 | 86, 72, 54, 41 | 83, 65, 47, 37 | — | — | — | —, 63, 48, 39 | — |
| | Cross-sectional increase, % at | | | | | | |
| 10 min. | — | — | — | — | — | — | 37$^b$ |
| 60 min. | — | — | 57$^a$ | — | 4$^a$ | 28$^a$ | 74$^b$ |
| 16 hrs. | 72$^a$ | — | — | — | — | — | — |

$^a$Using phosphate buffer at pH 7.2 and 37° C.
$^b$Using isotonic saline at 25° C.

EXAMPLE 4

Conversion of Polyether-Ester PI-S-6 to Monofilament Sutures and Evaluation of Their Properties Detailed extrusion and orientation conditions of PI-S-6 (from Example 1, Table II), and tensile properties of oriented monofilaments are summarized in Table VII.

TABLE VII

Extrusion of Polyester-ester PI-S-6 and Properties of Its Monofilament

| Temperature Profile During Extrusion, ° C. | | | | Orientation Scheme |
|---|---|---|---|---|
| Zone 1 | Zone 2 | Zone 3 | Spinhead | Draw Ratio/Temp, ° C. |
| 120 | 145 | 178 | 183 | 9-17/75-90 |

Polymer $T_m$ = 172° C.

| Diameter (mm) | Linear Max Load (N) | Linear Strength (kpsi) | Modulus (kpsi) | Elongation (%) | Knot Max Load (N) |
|---|---|---|---|---|---|
| 0.28 | 17 | 35 | 314 | 94 | 16 |
| 0.24 | 16 | 43 | 400 | 65 | 15 |

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicants hereby disclose all subranges of all ranges disclosed herein. These subranges are also useful in carrying out the present invention.

EXAMPLE 5

General Experimental Methods for Multifilament Spinning, Orientation, Braiding, and Tensile Testing The individual polymers were melt-spun into multifilament yarn using a multi-hold die, under slightly higher thermal conditions as compared to those used in the production of the monofilaments in Example 4. Depending on the required yarn denier, the extruded multifilament yarns were oriented in two stages at a temperature range of 60° C. to 85° C. Polyether-esters PII-F-3 and PII-F-4 were converted to braided multifilaments, and tested for their tensile properties using a MiniBionix MTS Universal Tester, Model 858. Braided multifilaments of polyether-esters PII-F-3 and PII-F-4, with diameters of 0.27 and 0.40 mm respectively, exhibited tensile strengths of 61.2 and 40.0 Kpsi and elongations of 34% and 52% respectively.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicants hereby disclose all subranges of all ranges disclosed herein. These subranges are also useful in carrying out the present invention.

What is claimed is:
1. A bioswellable braided coatable suture comprising multifilaments, the uncoated multifilaments comprising an absorbable polyether-ester, the polyether-ester comprising a polyether glycol end-grafted with at least one cyclic mono- mer selected from the group consisting of l-lactide, glycolide, p-dioxanone, trimethylene carbonate, ϵ-caprolactone, 1,5-dioxepan-2-one, and a morpholinedione, the individual filaments exhibiting at least 5% increase in cross-sectional area when placed in a biological environment.

2. A bioswellable braided multifilament suture as in claim 1 further comprising a surface coating comprising an ϵ-caprolactone copolymer.

3. A bioswellable braided coatable suture comprising: multifilaments consisting of an absorbable polyether-ester, the polyether-ester comprising a polyether glycol end-grafted with at least one cyclic monomer selected from the group consisting of l-lactide, glycolide, p-dioxanone, trimethylene carbonate, ϵ-caprolactone, 1,5-dioxepan-2-one, and a morpholinedione, the individual filaments exhibiting at least 5% increase in cross-sectional area when placed in a biological environment.

4. A bioswellable braided coatable suture as in claim 3 wherein the suture consists of multifilaments consisting of an absorbable polyether-ester, the polyether-ester comprising a polyether glycol end-grafted with at least one cyclic monomer selected from the group consisting of l-lactide, glycolide, p-dioxanone, trimethylene carbonate, ϵ-caprolactone, 1,5-dioxepan-2-one, and a morpholinedione, the individual filaments exhibiting at least 5% increase in cross-sectional area when placed in a biological environment.

5. A bioswellable braided coatable suture as in claim 3 wherein the polyether-ester comprises polyethylene glycol end-grafted with glycolide and ϵ-caprolactone.

6. A bioswellable braided coatable suture as in claim 3 wherein the polyether-ester comprises polyethylene glycol end-grafted with glycolide and trimethylene carbonate.

7. A bioswellable braided coatable suture as in claim 3 wherein the polyether-ester comprises polyethylene glycol end-grafted with glycolide and ϵ-caprolactone in a molar ratio of 18/82 polyethylene glycol//(70/30)glycolide-co-ϵ-caprolactone.

8. A bioswellable braided coatable suture as in claim 4 wherein the polyether-ester comprises polyethylene glycol end-grafted with glycolide and trimethylene carbonate in a molar ratio of 10/90 polyethylene glycol//(90/10 glycolide-co-trimethylene carbonate).

9. A bioswellable braided coatable suture as in claim 4 wherein the polyether-ester comprises polyethylene glycol end-grafted with glycolide and trimethylene carbonate in a molar ratio of 7/93 polyethylene glycol//(90/10 glycolide-co-trimethylene carbonate).

10. A bioswellable braided coatable suture as in claim 2 wherein the polyether-ester comprises polyethylene glycol end-grafted with glycolide and ϵ-caprolactone.

11. A bioswellable braided coatable suture as in claim 2 wherein the polyether-ester comprises polyethylene glycol end-grafted with glycolide and trimethylene carbonate.

12. A bioswellable braided multifilament suture comprising multifilaments consisting of an absorbable polyether-ester, the polyether-ester comprising a polyether glycol end-grafted with at least one cyclic monomer selected from the group consisting of l-lactide, glycolide, p-dioxanone, trimethylene carbonate, ϵ-caprolactone, 1,5-dioxepan-2-one, and a morpholinedione, the individual filaments exhibiting at least 5% increase in cross-sectional area when placed in a biological environment and a surface coating comprising an ϵ-caprolactone copolymer.

\* \* \* \* \*